US007176685B2

(12) United States Patent
Blasche

(10) Patent No.: US 7,176,685 B2
(45) Date of Patent: Feb. 13, 2007

(54) IMAGING MEDICAL DIAGNOSIS APPARATUS AND METHOD FOR THE OPERATION OF A MAGNETIC RESONANCE APPARATUS

(75) Inventor: Mathias Blasche, Buckenhof (DE)

(73) Assignee: Siemens Aktiengesellschaft, Munich (DE)

( * ) Notice: Subject to any disclaimer, the term of this patent is extended or adjusted under 35 U.S.C. 154(b) by 701 days.

(21) Appl. No.: 10/288,127

(22) Filed: Nov. 5, 2002

(65) Prior Publication Data
US 2003/0086598 A1 May 8, 2003

(30) Foreign Application Priority Data
Nov. 8, 2001 (DE) ................................ 101 54 799

(51) Int. Cl.
G01V 3/00 (2006.01)
G06K 9/00 (2006.01)

(52) U.S. Cl. ...................... 324/309; 382/128
(58) Field of Classification Search ................ 324/307; 382/128; 345/629; 342/109; 378/59
See application file for complete search history.

(56) References Cited

U.S. PATENT DOCUMENTS

| | | | | |
|---|---|---|---|---|
| 4,855,910 A | * | 8/1989 | Bohning | ...................... 324/309 |
| 5,121,470 A | * | 6/1992 | Trautman | ................... 345/440 |
| 5,474,067 A | | 12/1995 | Laub | |
| 5,719,498 A | | 2/1998 | Hausmann | |
| 5,803,914 A | | 9/1998 | Ryals et al. | |
| 5,995,108 A | | 11/1999 | Isobe et al. | |
| 6,275,035 B1 | * | 8/2001 | Debbins et al. | ............. 324/307 |
| 6,301,497 B1 | * | 10/2001 | Neustadter | ................... 600/410 |
| 6,380,740 B1 | | 4/2002 | Laub | |
| 6,381,487 B1 | | 4/2002 | Flohr et al. | |
| 6,522,141 B2 | * | 2/2003 | Debbins et al. | ............. 324/307 |
| 6,614,453 B1 | * | 9/2003 | Suri et al. | .................... 715/764 |
| 6,801,037 B1 | * | 10/2004 | Zhang | ......................... 324/309 |
| 6,844,884 B2 | * | 1/2005 | Balloni et al. | ............... 345/629 |
| 2002/0024340 A1 | * | 2/2002 | Debbins et al. | ............. 324/307 |
| 2003/0052879 A1 | | 3/2003 | Barth et al. | |

OTHER PUBLICATIONS

"Bildgebende Systeme für die Medizinische Diagnostik," Morneburg (1995), pp. 544-557.

* cited by examiner

Primary Examiner—Matthew C. Bella
Assistant Examiner—Utpal Shah
(74) Attorney, Agent, or Firm—Schiff Hardin LLP

(57) ABSTRACT

An imaging medical diagnosis apparatus has a display and operating device in which raw data of a region of an examination subject to be images can be stored, and an actuator with which a grouping of raw data can be defined, displayable at the display and operating device. In a method for operating a magnetic resonance apparatus at least two raw data sets divided into segments are generated in a time sequence from the same region of an examination subject and are stored in the diagnosis apparatus, and segments from both raw datasets that have been generated during a selectable time span of the time sequence are grouped to form a further raw dataset.

13 Claims, 3 Drawing Sheets

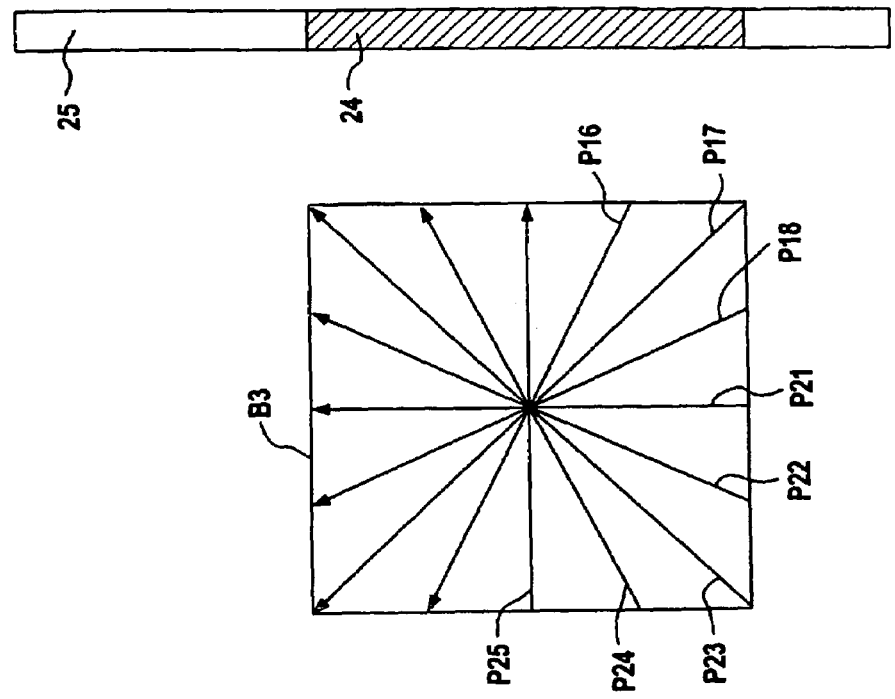
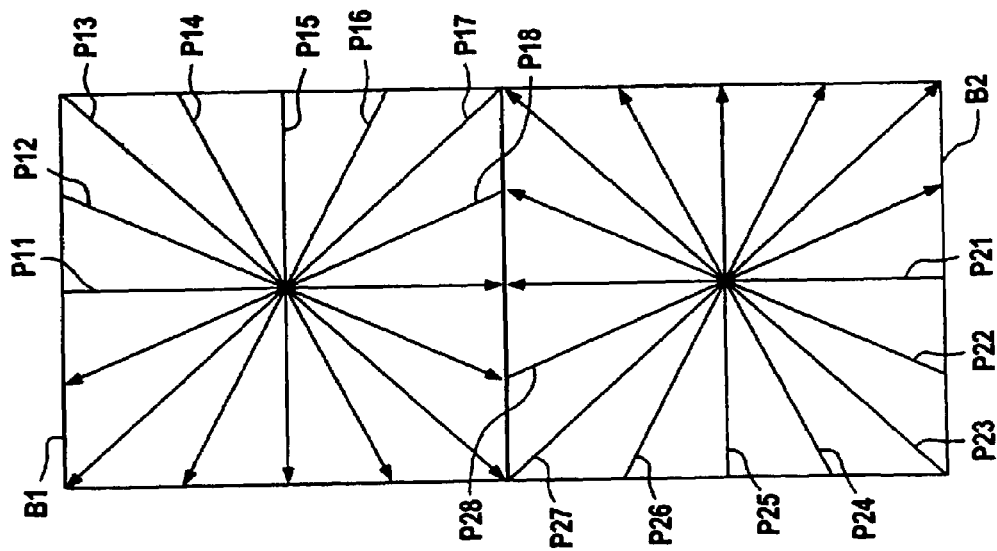
FIG 3

IMAGING MEDICAL DIAGNOSIS APPARATUS AND METHOD FOR THE OPERATION OF A MAGNETIC RESONANCE APPARATUS

BACKGROUND OF THE INVENTION

1. Field of the Invention

The invention is directed to an imaging medical diagnosis apparatus and to a method for the operation of a magnetic resonance apparatus.

2. Description of the Prior Art

Ultrasound apparatus, X-ray computed tomography and magnetic resonance imaging are utilized as imaging medical diagnosis modalities. Magnetic resonance technology is a known technique for, among other things, acquiring images of the inside of the body of an examination subject. In a magnetic resonance apparatus, rapidly switched gradient fields that are generated by a gradient system are superimposed on a static basic magnetic field that is generated by a basic field magnet system. Further, a magnetic resonance apparatus has a radiofrequency system that emits radiofrequency signals into the examination subject for triggering magnetic resonance signals, and picks up the resulting magnetic resonance signals. Magnetic resonance images are produced on the basis of these signals.

For operation of a magnetic resonance apparatus, time curves for currents in the gradient system, radiofrequency transmission pulses and sampling periods for magnetic resonance signals are matched to one another. This is implemented in a control system of the magnetic resonance apparatus on the basis of a prescribable sequence.

In various areas of employment of an imaging medical diagnosis apparatus, there is a need to repeatedly image the same region of the examination subject in rapid succession and with a high time resolution. In magnetic resonance technology, this is especially true of dynamic perfusion measurements, dynamic angiographies supported by a contrast agent, and dynamic contrast agent studies, for example in mammography. A number of methods are known with which a time resolution that is mainly limited by a maximum speed of the gradient system can be enhanced, particularly given dynamic measurements.

Thus, for example, planar imaging methods can be designed significantly more efficiently when a number of neighboring slices are acquired time-offset instead of acquiring the layers successively. This is especially advantageous given sequences wherein a time span for the excitation, location encoding and magnetic resonance signal detection for a slice is significantly shorter than a repetition time, so that the difference between the repetition time and the time span can be utilized for further layers for implementing excitation, location encoding and magnetic resonance signal detection. Further details about this are described, for example, in the book by H. Morneburg, "Bildgebende Systeme für die medizinische Diagnostik", Publicis MCD Verlag, Erlangen, 1995, pages 544–548.

For example, an echo multiple use technique is known in connection with multi-echo sequences. In one echo train, the data of at least one echo of the same region entered in the edge region of a first raw data matrix as well as the edge region of a second raw data matrix, and only the respective central regions of the matrices are occupied with data from different echoes. Such a multiple use of an echo for the production of two raw data matrices, for example with different contrast properties, enables a time-saving. Further details about this are described, for example, in the above book on pages 549–557.

U.S. Pat. No. 4,327,325 also discloses a method for time-resolved magnetic resonance imaging, wherein signals are acquired by excitation and phase coding of nuclear spins, the signals being entered row-by-row into a raw data matrix divided into individual segments. An image is produced from every completely occupied raw data matrix, with a motion sequence of a number of images being obtained by acquiring a number of raw data matrices at different points in time. Signals of at least one segment are employed for two temporally successive raw data matrices and the measurement time thus can be shortened.

In a method for operating a magnetic resonance apparatus, German OS 199 24 448 discloses, for improved location/tome resolution, dividing the three-dimensional Fourier space in a phase-coding direction of a sequence into annular segments, with the phase encoding steps being defined in terms of the time sequence such that the central segment of the Fourier space is covered more often than outer segments.

SUMMARY OF THE INVENTION

An object of the present invention is to provide an improved imaging medical diagnosis apparatus and an improved method for the operation of a magnetic resonance apparatus with which—among other things—good post-processing of raw data stored in the apparatus can be achieved.

This object is inventively achieved in an imaging medical diagnosis apparatus having a display and operating device wherein raw data of a region of an examination subject to be images can be stored and an actuator, with which a grouping of raw data can be defined, is displayable at the display and operating device.

As a result, post-processing of raw data stored in the diagnosis apparatus that is flexible and can be controlled by an operator in a simple way is achieved.

In the inventive method for operating a magnetic resonance apparatus at least two raw data sets divided into segments are generated in a time sequence from the same region of an examination subject to be imaged and are stored in the diagnosis apparatus, and segments from both raw datasets that have been generated during a selectable time span of the time sequence are grouped to form a further raw dataset.

In a simple way and with a fine time resolution, that is limited only by the extent to which exposure points in time or exposure time durations can be allocated to individual raw data or groups of raw data, an operator of the magnetic resonance apparatus can select a time span of the sequence that, for example, has a high diagnostic effect in view of the diagnosis to be produced.

DESCRIPTION OF THE DRAWINGS

FIG. 3 illustrates a grouping of raw data from two raw data sets for a first part and a second part of a region to be imaged, the second part adjoining the first part, in accordance with the invention.

DESCRIPTION OF THE PREFERRED EMBODIMENTS

Figure 1:
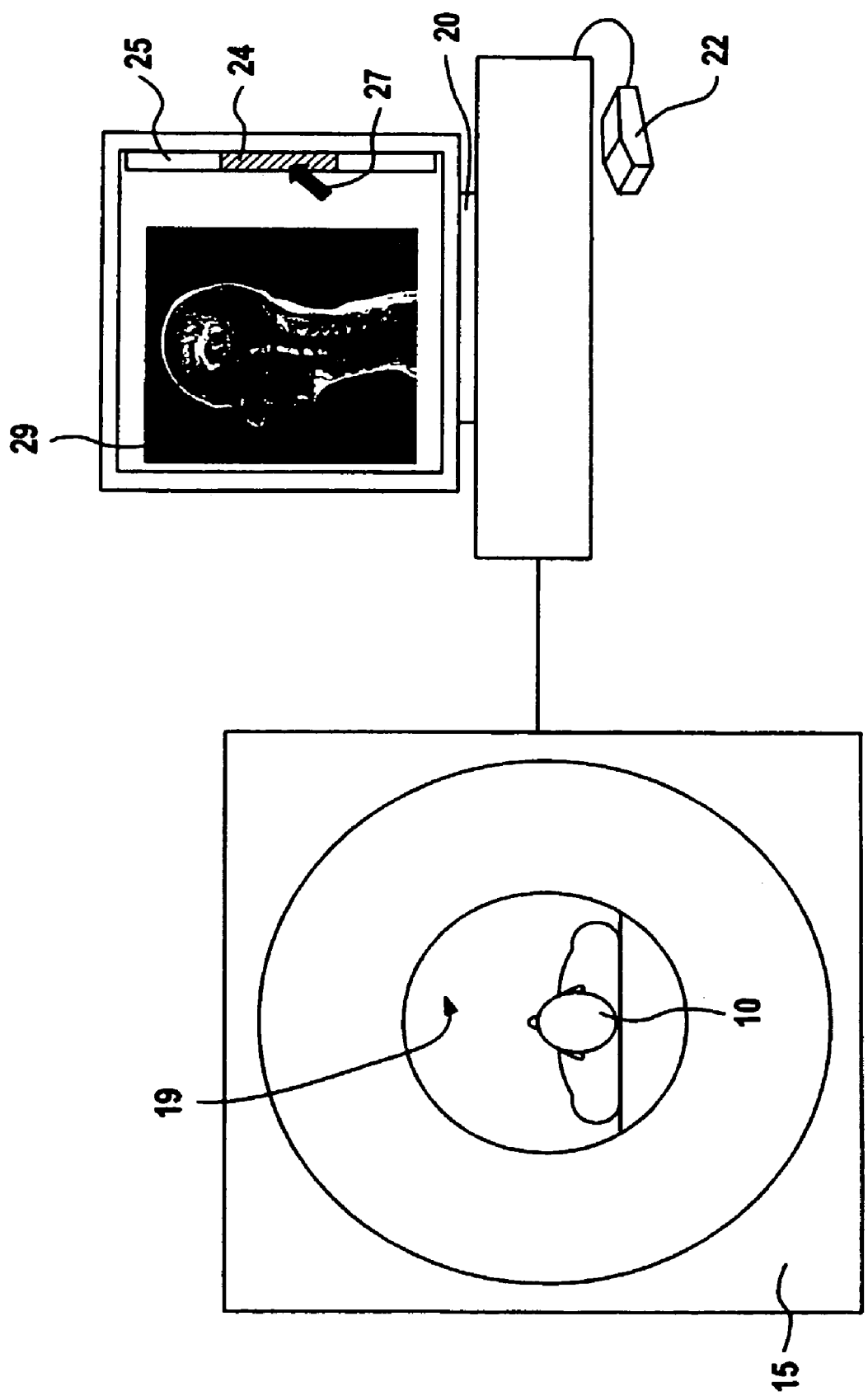
FIG. 1 schematically illustrates an imaging medical diagnosis apparatus with a display and operating device in accordance with the invention.

As an exemplary embodiment of the invention, FIG. 1 shows an imaging medical diagnosis apparatus with a display and operating device 20. For a region of an examination subject to be imaged, for example the head of a patient 10 that is placed in the examination space 19 of a base unit 15 of the diagnosis apparatus, raw data of the region to be imaged can be registered with the diagnosis apparatus. The raw data, from which images of the region to be imaged can be reconstructed and displayed at the display and operating device 20, are stored in the diagnosis apparatus.

When the diagnosis apparatus is a magnetic resonance apparatus, then the raw data are generated in the Fourier domain and stored. When, in contrast, the apparatus is an X-ray computed tomography apparatus, then the raw data are generated as projection data in the image domain and stored.

In addition to a medical diagnostic image 29 that can be reconstructed from raw data, for example a sagittal tomogram of the head of the patient 10, an image bar 25 with an image pan field 24 displaceable therein also can be displayed at the display and operating device 20. An operator of the diagnosis apparatus working at the display and operating device 20 can displace the image pan field 24 within the image pan bar 25 with a computer mouse 22 of the display and operating device 20 and a mouse pointer 27 correspondingly displayed at the display and operating device 20. To that end, a tip of the mouse pointer 27 is positioned in the image pan field 24 by means of a corresponding movement of the computer mouse 22, the image pan field 24 is clicked on with a key of the computer mouse 22, and is correspondingly dragged in the clicked-on condition by movement of the computer mouse 22.

At least two raw datasets of a same region to be imaged, that are registered in a temporal sequence, for example a dynamic measurement, are stored in the diagnosis apparatus. When the raw data sets are generated with an exposure technique wherein appertaining exposure points in time or exposure time durations can be allocated to the individual raw data or groups of raw data, then a time span within the temporal sequence can be determined with a displacement of the image pan field 24. Parts from both raw data sets, the parts each containing raw data registered during the defined time span, are grouped. A new image can then be reconstructed and displayed from the newly grouped raw dataset. The raw data thus can be flexibly post-processed and, for example, snapshots can be defined. Further, a practically arbitrarily fine time resolution can be realized, this being particularly advantageous for achieving a high time resolution in conjunction with the techniques described above. Further details are described in FIG. 2 in the form of an exemplary embodiment.

Corresponding images are continuously displayed with the displacement of the image pan field 24, so that the user has the interactive ability to identify the medical diagnostic image of that time span that offers the maximum informational content within a dynamic event. An example of this is the optimum capture of the arterial phase without venous overlay in contrast agent-supported magnetic resonance angiography.

When at least one first raw dataset for a first part of the region to be imaged and a second raw dataset for a second part of the region to be imaged that adjoins said first part are stored in the diagnosis apparatus, for example in a X-ray computed tomography apparatus, then a further part of the region to be imaged that is located between the first part and the second part, can be selected with the displacement of the image pan field 24. For this, the raw data from the two raw data sets that are spatially allocated to the further part are grouped into a new raw dataset that is reconstructed and displayed. Further details of this are described as an example in FIG. 3. With the displacement of the image pan field 24, corresponding images are continuously displayed, so that the operator has the interactive ability, for example, of determining the tomogram that is the most diagnostically significant for the particular diagnostic task, in terms of a spatial position within the region to be imaged.

Figure 2:
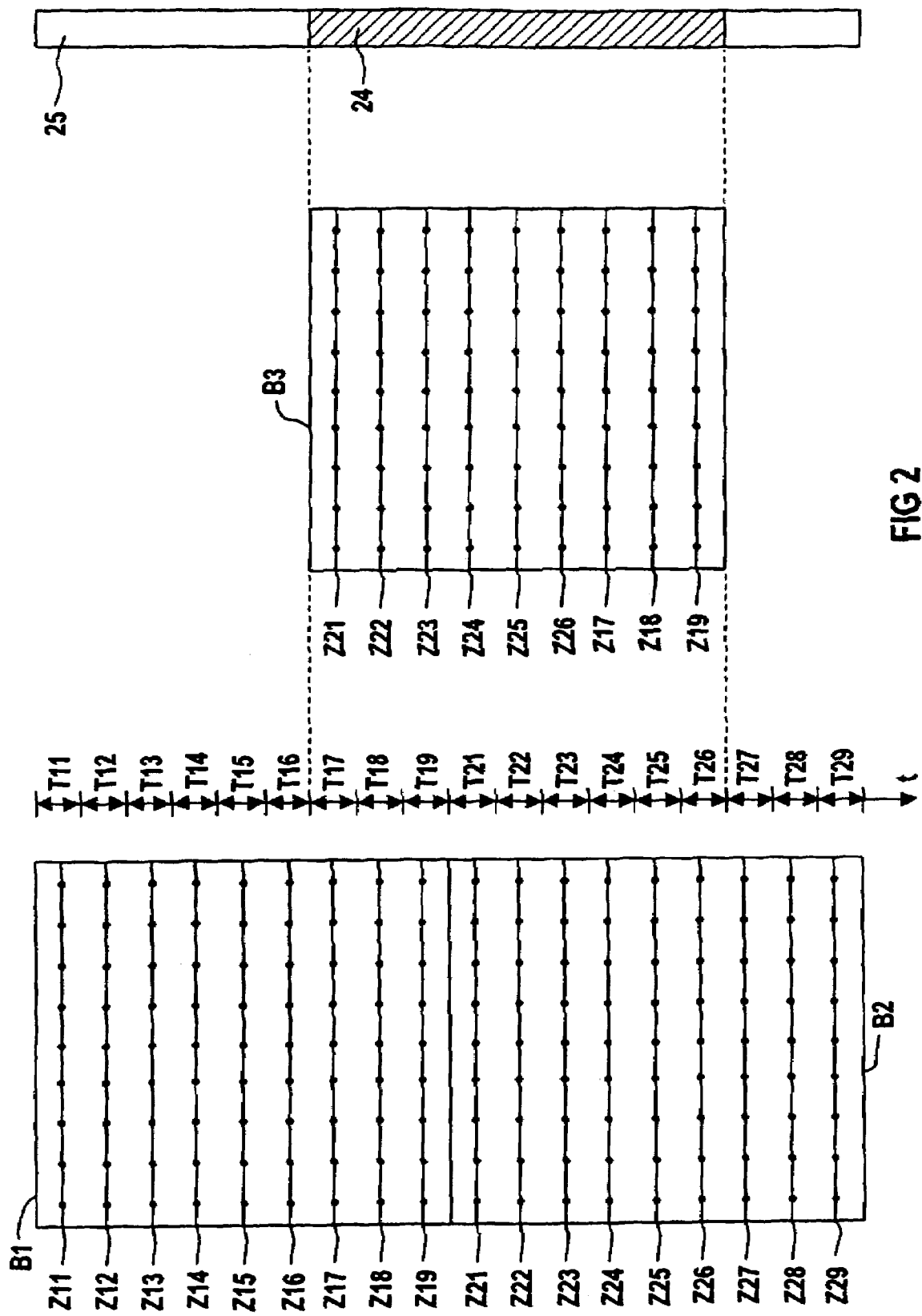
FIG. 2 illustrates a grouping of raw data from two raw data sets of a same region to be imaged registered in a temporal succession in accordance with the invention.

As an exemplary embodiment of the invention, FIG. 2 shows a grouping of raw data from two raw datasets B1 and B2 of a same region to be imaged that are registered in a time sequence. The raw datasets B1 and B2 registered immediately successive in time are two-dimensional datasets of the Fourier domain that were generated with a magnetic resonance apparatus using a sequence for the row-by-row filling of the raw datasets B1 and B2. The rows Z11 through Z19 of the first dataset B1 are occupied with data during the time durations T11 through T19 and the lines Z21 through Z29 of the second dataset B2 are occupied with data during the time durations T21 through T29.

With a displacement of the image pan field 24 within the image pan bar 25, which are again shown in FIG. 2 for clarity, the operator can define a time span for which parts from the two raw datasets B1 and B2 that were registered during the defined time span are grouped to form a further raw dataset B3. A time duration for a registration of one of the raw datasets B1 and B2, which is equal to the time durations T11 through T19 or T21 through T29, usually defines an expanse of the image pan field 24 in the displacement direction so that a complete filling of the newly grouped raw dataset B3 is achieved.

A time span from T17 through T26 is selected according to the illustration in FIG. 2, so that the rows Z21 through Z26 of the second raw dataset B2 occupied with data during the time durations T21 through T26 are employed for the first six rows of the further raw dataset B3, and the rows Z17 through Z19 of the first raw dataset B1 occupied with data during the time durations T17 through T19 are employed for the last three lines of the further raw dataset B3. The raw dataset B3 compiled in this way is reconstructed and correspondingly displayed at the display and operating device 20 as an image of the region in question.

In the exemplary embodiment according to FIG. 2, an even finer time resolution for the time spans to be defined can be achieved by allocating a point in time, at which the respective data point was acquired, to each data point of each row Z11 through Z29 of the raw datasets B1 and B2. As a result, not only can complete rows Z11 through Z29 be grouped to form a further raw dataset but the individual data points can be accessed for this purpose.

In the description set forth in FIG. 2 as an example for two-dimensional raw datasets registered row-by-row can be correspondingly applied to other instances, for example to more raw datasets, three-dimensional raw datasets that have been generated, for example, in the framework of a multiple 3D measurement, raw datasets that are occupied with data with segmented spiral or, respectively, radial techniques or with a projection method, etc.

As an exemplary embodiment of the invention, FIG. 3 shows a grouping of raw data from a first raw dataset D1 for a first part of a region to be imaged and from a second raw dataset D2 for a second part of the region to be imaged that adjoins the first. The raw datasets D1 and D2 are generated as datasets of the image space with an X-ray computed tomography apparatus. A first tomogram of the region to be imaged can be reconstructed from the first raw dataset D1 and a second tomogram of the region to be imaged can be reconstructed from the second raw dataset D2, the second tomogram adjoining the first.

For generating raw data, the region to be imaged can be considered as being fixed by the X-ray computed tomography apparatus, i.e. by the transmission and reception unit of the X-ray computed tomography apparatus that rotates on a helical path around the region to be imaged. Eight projection exposures P11 through P18 are generated for the first raw dataset D1 during a first revolution of the transmission and reception unit by 180° plus fan angle, and another eight projection exposures P21 through P28 are generated for the second raw dataset D2 during a second revolution that immediately follows the first revolution. Larger partial revolutions or complete revolutions can be employed in other embodiments.

Further slice positions between the slice positions defined by the raw datasets D1 and D2 can be selected with a displacement of the image pan field 24 within the image pan bar 25, which are again shown in FIG. 3 for clarity. Corresponding to the position of the image pan field 24 within the image pan bar 25 shown in FIG. 3, a further raw dataset D3 is grouped from the projection exposures P16 through P18 of the first raw dataset D1 and the projection exposures P21 through P25, reconstructed and displayed at the display and operating device 20. An optimum slice position with reference to the anatomy of interest can thus be displayed.

When the raw datasets D1 and D2 described in FIG. 3 are two raw datasets from the same region that have been registered in immediate temporal succession with a magnetic resonance apparatus using a radial technique, then the displacement of the image pan field 24, similar to the case of FIG. 2, defines a time span for which parts from the two raw datasets D1 and D2 that have been registered during the defined time span are grouped to form a further raw dataset.

Although modifications and changes may be suggested by those skilled in the art, it is the intention of the inventor to embody within the patent warranted hereon all changes and modifications as reasonably and properly come within the scope of his contribution to the art.

I claim as my invention:

1. An imaging medial diagnosis apparatus comprising:
   a memory in which raw data obtained from a region of an examination subject to be imaged are stored;
   a display and operating device having access to said memory, said display and operating device displaying an actuator, adapted for actuation by a user, to define groupings of said raw data;
   a data acquisition device for acquiring at least two raw datasets of said region in a time sequence, each of said at least two raw datasets being stored in said memory; and
   said actuator defining a time span of said time sequence for which parts of said at least two raw datasets registered during said time span are grouped.

2. An imaging medical diagnosis apparatus as claimed in claim 1 further comprising a computer for reconstructing an image from the grouped raw data, and wherein said operating and display device displays said image.

3. An imaging medical diagnosis apparatus as claimed in claim 2 wherein said display and operating device continuously displays said image as said actuator is actuated, with said image changing as said actuator is actuated.

4. An imaging medical diagnosis apparatus as claimed in claim 1 wherein said actuator includes a displayed image pan field within an image pan bar, and wherein said grouping of said raw data is dependent on a position of said image pan field within said image pan bar defined by displacement of said image pan field.

5. An imaging medical diagnosis apparatus as claimed in claim 1 comprising:
   a data acquisition device which obtains a first raw dataset for a first part of said region and a second raw dataset for a second part of said region, said second part adjoining said first part, and wherein said first and second raw datasets are stored in said memory; and
   wherein actuation of said actuator defines a further part of said region between said first and second parts by grouping respective parts from said first raw dataset and said second raw dataset.

6. An imaging medical diagnosis apparatus as claimed in claim 1 wherein said raw data stored in said memory are image domain data.

7. An imaging medical diagnosis apparatus as claimed in claim 1 wherein said raw data stored in said memory are Fourier domain data.

8. An imaging medical diagnosis apparatus as claimed in claim 1 comprising a magnetic resonance data acquisition system for acquiring said raw data.

9. An imaging medical diagnosis apparatus as claimed in claim 1 comprising an x-ray computed tomography system for obtaining said raw data.

10. A method for operating a magnetic resonance apparatus, comprising the steps of:
    obtaining at least two raw datasets, divided into segments, in a time sequence from the same region of an examination subject;
    storing said at least two raw datasets; and
    displaying an actuator at a display device and selecting a time span within said time sequence, by actuating said actuator at said display device, and grouping segments from said at least two raw datasets obtained during the selected time span to form a further raw dataset.

11. A method as claimed in claim 10 comprising reconstructing an image of said region from said further raw dataset and displaying said image, at said display device.

12. A method as claimed in claim 10 comprising continuously displaying images of said region at said display device as said actuator is actuated at said display device, said images changing dependent on said actuation of said actuator.

13. A method as claimed in claim 10 wherein the step of displaying said actuator comprises displaying an image pan field within an image pan bar and grouping said raw data by displacing said image pan field within said image pan bar at said display device.

* * * * *